United States Patent
Asano et al.

(10) Patent No.: US 7,916,921 B2
(45) Date of Patent: Mar. 29, 2011

(54) OSTEOPOROSIS DIAGNOSIS SUPPORT DEVICE

(75) Inventors: Akira Asano, Higashihiroshima (JP); Akira Taguchi, Hiroshima (JP); Takashi Nakamoto, Hiroshima (JP); Keiji Tanimoto, Hiroshima (JP); Zainal Arifin Agus, Higashihiroshima (JP)

(73) Assignee: Hiroshima University Independent Administrative Agency, Higashihiroshima-shi (JP)

( * ) Notice: Subject to any disclaimer, the term of this patent is extended or adjusted under 35 U.S.C. 154(b) by 965 days.

(21) Appl. No.: 11/665,710

(22) PCT Filed: Oct. 18, 2005

(86) PCT No.: PCT/JP2005/019078
§ 371 (c)(1),
(2), (4) Date: Jun. 4, 2007

(87) PCT Pub. No.: WO2006/043523
PCT Pub. Date: Apr. 27, 2006

(65) Prior Publication Data
US 2007/0286467 A1    Dec. 13, 2007

(30) Foreign Application Priority Data
Oct. 19, 2004    (JP) ................................ 2004-304855

(51) Int. Cl.
*G06K 9/00* (2006.01)
(52) U.S. Cl. ........................................ 382/132; 382/199
(58) Field of Classification Search .................. 382/128, 382/132, 199; 378/38, 54, 55, 62
See application file for complete search history.

(56) References Cited

U.S. PATENT DOCUMENTS
2006/0239532 A1 * 10/2006 Taguchi et al. ............... 382/132

FOREIGN PATENT DOCUMENTS

| JP | 08-215196 A | 8/1996 |
|---|---|---|
| JP | 11-313820 A | 11/1999 |
| JP | 2004-113484 A | 4/2004 |
| JP | 2004-209089 A | 7/2004 |
| WO | WO-03/049615 A1 | 6/2003 |
| WO | WO 2004/060165 A1 * | 7/2004 |

* cited by examiner

OTHER PUBLICATIONS

Jun'ichi Otogoto et al., "Panorama X-sen Shashin Parameter o Mochiita Shishubyo to Kotsu Soshosho no Kankei no Kento Oyobi Kotsu Soshosho Shindan no Kokoromi", Journal of the Japanese Society of Periodontology, 2001, vol. 43, No. 1, pp. 13 to 24.

*Primary Examiner* — Andrew W Johns
(74) *Attorney, Agent, or Firm* — Birch, Stewart, Kolasch & Birch, LLP

(57) ABSTRACT

It can be enabled an accurate diagnosis of osteoporosis by a simple method utilizing panoramic radiographs without requiring special skill or experience of a technician engaged in diagnosis of osteoporosis. It comprises an object region image acquisition means for enhancing the contrast of a mandible bone on digitized panoramic radiographs and extracting a portion of a mandible including a mental foramen and a mandibular base as an object region image; a discrimination and selection means for discriminating between a background portion and the portion of a mandible from the object region image and acquiring, as a judgment region image, a portion from which the background portion is removed; a defined image acquisition means for defining forms of a cortical bone and a cancellous bone constituting the mandible of the judgment region image; a means for specifying the cortical bone portion on the image in which the form is defined; calculation means for determining the thickness of the cortical bone based on the outline constituting the mental foramen and the cortical bone specified by the respective means; and an output means for outputting the determined thickness of the cortical bone.

8 Claims, 6 Drawing Sheets

OSTEOPOROSIS DIAGNOSIS SUPPORT DEVICE

TECHNICAL FIELD

The present invention relates to an osteoporosis diagnosis support device for performing an osteoporosis diagnosis using panoramic radiographs taken in a dental treatment.

BACKGROUND ART

The number of osteoporosis patients is increasing with increasing in aged population, and public concern is now focused on osteoporosis. In this circumstance, an osteoporosis examination is one of objectives of the Law of Health and Medical Services System for the Aged and has been made by various medical facilities including a public health center.

The osteoporosis examination uses the DXA method which can measure a bone mass of a lumbar vertebra, radius, and femur neck by dual energy X-ray, the MD method which measures a bone mass of the cortical bone of the metacarpal bone by dual energy X-ray, or a ultrasonic method which uses no X-rays. The DXA method can perform an accurate diagnosis based on detailed data, but requires an expensive and large device. The MD method or the ultrasonic method can simply make a measurement, but is poor in accuracy. In particular, the ultrasonic method causes a large measurement error.

Therefore, an osteoporosis diagnosis method or device which can simply and accurately make a measurement has been required. As for the ultrasonic method, Patent Document 1 or 2 discloses an osteoporosis diagnosis device and method which can improve a measurement accuracy of a bone density. On the other hand, the advancement of the medical study on osteoporosis has revealed that a form of the cortical bone of a mandible forming a mandibular bone is changed with a lowered bone density, and Patent Document 3 discloses an osteoporosis diagnosis support device using panoramic radiographs performed in a dental treatment as means judging the presence or absence of osteoporosis from the changed state of the form of the cortical bone of the mandible.

Patent Document 1: JP-A-8-215196
Patent Document 2: JP-A-11-313820
Patent Document 3: JP-A-2004-209089

DISCLOSURE OF INVENTION PROBLEM WHICH THE INVENTION IS TO SOLVE

However, the osteoporosis diagnosis device or method based on the ultrasonic method disclosed in Patent Document 1 or 2 is required to improve measurement accuracy and cannot easily improve the measurement accuracy due to its measurement principle. To the contrary, the osteoporosis diagnosis support device using panoramic radiographs can perform an osteoporosis diagnosis using panoramic radiographs performed in a dental treatment. Therefore, the osteoporosis diagnosis support device is promising for a prevention or medical care service support expected for a medical treatment in the future, not only for conventional medical treatment treating sick person. However, the osteoporosis diagnosis support device is required to improve a measurement accuracy and to simplify a measurement means.

The present invention has been made in view of such prior art problems and public requirement and an object of the present invention is to propose an osteoporosis diagnosis support device which permits an accurate osteoporosis diagnosis by a simple method using panoramic radiographs without requiring any special skill and experience of a technician involved in the osteoporosis diagnosis.

Means To Solve The Problem

An osteoporosis diagnosis support device according to the present invention comprises: an object region image acquisition unit for acquiring image data of panoramic radiographs including a cortical bone; an outline acquisition unit for acquiring a pixel group A forming an outer edge of the cortical bone in the image data and a pixel group B forming an inner edge of the cortical bone in the image data; a calculation unit for using, as a reference point, a specific point which is a point in the image data and is different from the pixel groups A and B to calculate a distance between a specific pixel in the pixel group A and a pixel in a predetermined range in the pixel group B; and an output unit for outputting the distance determined by the calculation unit as a thickness of the cortical bone.

In the above invention, the reference point may be determined to be the mental foramen of the mandible. The calculation unit comprises an outer edge point specification unit for specifying, as an outer edge point, the specified pixel, in which an angle formed by a regression line based on one pixel constituting the pixel group A and a pixel therenear and a straight line connecting the reference point and the specific pixel is closest to 90°; an inner edge point specification unit specifying, as an inner edge point, the pixel group B within a fixed distance from a straight line connecting the reference point and the outer edge point; and a length calculation unit calculating the distance from the outer edge point to the inner edge point.

The thickness of the cortical bone can be the smallest value, the largest value, or the average value of the distance determined by the calculation unit.

An osteoporosis diagnosis support method according to the present invention comprises: an object region image acquisition step for acquiring image data of a panoramic radiograph including a cortical bone; an outline acquisition step for acquiring a pixel group A forming an outer edge of the cortical bone in the image data and a pixel group B forming an inner edge of the cortical bone in the image data; a calculation step using, as a reference point, a specific point which is a point in the image data and is different from the pixel groups A and B to calculate a distance between a specific pixel in the pixel group A and a pixel within a predetermined range in the pixel group B; and an output step for outputting the distance determined by the calculation step as a thickness of the cortical bone.

An osteoporosis diagnosis support program according to the present invention comprises: an object region image acquisition program for acquiring image data of panoramic radiographs including a cortical bone; an outline acquisition program for acquiring a pixel group A forming an outer edge of the cortical bone in the image data and a pixel group B forming an inner edge of the cortical bone in the image data; a calculation program using, as a reference point, a specific point which is a point in the image data and is different from the pixel groups A and B to calculate a distance between a specific pixel in the pixel group A and a pixel in a predetermined range in the pixel group B; and an output program for outputting the distance determined by the calculation program as a thickness of the cortical bone.

An osteoporosis diagnosis support LSI according to the present invention comprises: an object region image acquisition unit for acquiring image data of panoramic radiographs including a cortical bone; an outline acquisition unit for acquiring a pixel group A forming an outer edge of the cortical bone in the image data and a pixel group B forming an inner edge of the cortical bone in the image data; a calculation unit using, as a reference point, a specific point which is a point in the image data and is different from the pixel groups A and B to calculate a distance between a specific pixel in the pixel group A and a pixel in a predetermined range in the pixel group B; and an output unit for outputting the distance determined by the calculation unit as a thickness of the cortical bone.

In addition, the present invention can be made as follows. An osteoporosis diagnosis support device according to the present invention comprises: an object region image acquisition means for enhancing contrast of a mandible bone on digitized panoramic radiographs and extracting a portion of a mandible including a mental foramen and a mandibular base as an object region image; a discrimination and selection means for discriminating between a background portion and the portion of a mandible from the object region image and acquiring, as a judgment region image, a portion in which the background portion is removed; a defined image acquisition means for defining forms and outlines of a cortical bone and a cancellous bone constituting the mandible of the judgment region image; a means for specifying a portion of the cortical bone on the image in which forms are defined; a calculation means for determining the thickness of the cortical bone based on an outline constituting the mental foramen and the cortical bone specified by the respective means; and an output means for outputting the determined thickness of the cortical bone.

In the present invention, the discrimination and selection means is preferably a program performing binarization processing comprising the following algorithms. That is, (1) a histogram of pixel values constituting an object region is created to sort, in ascending order, the pixel values appearing in the histogram. Here, a group of pixels belonging to one pixel value constitutes one cluster. (2) A distance between two adjacent clusters is measured to combine the pair at the smallest distance into a cluster having a smaller pixel value. (3) The above operation is repeated to advance cluster combination until it becomes two clusters. (4) In the two clusters obtained in (3), the pixel values belonging to the cluster having a larger pixel value are all replaced with 1 (white), and the pixel values belonging to the cluster having a smaller pixel value are all replaced with 0 (black). A distance between clusters is defined as the product of intra-cluster dispersion and inter-cluster dispersion.

The calculation means is preferably a program comprising the following algorithms. That is, (1) With one point belonging to the specified cortical bone as a start point, a straight line is extended in a direction in which the x coordinate is increased in parallel with the y coordinate, and a pixel at the point crossing the outline is stored in a storage area. (2) A pixel on the outline within 8 pixels near each pixel in the storage area is stored in the storage area. (3) Further, a pixel on the outline within 8 pixels near each pixel is stored in the storage area. Such operation is repeated one after another and is continued until there are no pixels to be stored in the storage area or a number of pixels in the storage area is the initially set value. (4) A pixel group A in the storage area forms an outer edge of the cortical bone. When there are pixels in the storage area having the same y coordinate, the pixel having the largest x coordinate forms the outer edge of the cortical bone. (5) With one point belonging to the specified cortical bone as a start point, a straight line is extended in the direction in which the x coordinate is decreased in parallel with the y coordinate, and a pixel crossing the outline is stored in the storage area to perform the same operation as (2) to (4) so that a pixel group B in the storage area forms the inner edge of the cortical bone. (6) A regression line based on each pixel in the pixel group A and a pixel therenear is determined. (7) An angle formed by a straight line connecting the mental foramen and the pixel in the pixel group A and the regression line based on the pixel is determined to specify, as an outer edge point, the pixel in which the angle is closest to 90°. (8) In the pixel group B within a fixed distance from a straight line connecting the outer edge point and the mental foramen, the point in which the distance between it and the outer edge point is smallest is an inner edge point. (9) A length from the outer edge point to the inner edge point is the thickness of the cortical bone. The y coordinate is the coordinate in the upward direction from the bottom, that is, in the direction from the foot to the head of a human body, when panoramic radiographs are taken, and the x coordinate is orthogonal to the y coordinate so that its positive direction is the direction moved away from the edge of the jaw.

The means for specifying the cortical bone portion preferably comprises an external input means of a mouse or a light pen, and a program for specifying the cortical bone portion based on a signal inputted from the external input means.

Further, in the above invention, an osteoporosis database, and a means for comparing data stored in the database with the thickness of the cortical bone to perform an osteoporosis identification diagnosis is preferably provided.

An osteoporosis diagnosis support device according to the present invention can be easily configured using a computer readable recording medium which records the following programs. That is, the computer readable recording medium comprises: (1) a program for enhancing the contrast of the mandible on digitized panoramic radiographs and extracting a portion of the mandible including the mental foramen and the mandibular base as an object region image; (2) a discrimination and selection program for discriminating between a background portion and the portion of the mandible from the object region image and acquiring, as a judgment region image, a portion from which the background portion is removed; (3) a program for defining the form and outline of the cortical bone and the cancellous bone constituting the mandible of the judgment region image; (4) a program for specifying a pixel belonging to the cortical bone based on a signal from external input means; (5) a program for determining the thickness of the cortical bone based on the outline forming the mental foramen and the cortical bone specified by the respective programs; and (6) a program for outputting the determined thickness of the cortical bone.

EFFECT OF INVENTION

The osteoporosis diagnosis support device according to the present invention can perform accurate osteoporosis diagnosis by a simple method using panoramic radiographs generally taken in dental treatment without requiring any special skill and experience of an operator involved in osteoporosis diagnosis. It is expected to provide osteoporosis prevention or the improvement of medical care service in conjunction with dental facilities and associated medical facilities.

DESCRIPTION OF NUMERALS

| | |
|---|---|
| 10 | Mandible bone |
| 12 | Mandibular |
| 121 | Mandibular base |
| 13 | Cortical bone |
| 14 | Cancellous bone |
| 16 | Second premolar tooth of mandible |
| 18 | Mental foramen |
| 100 | Object region image acquisition means |
| 110 | Discrimination and selection means |
| 120 | Defined image acquisition means |
| 130 | Specifying the cortical bone portion means |
| 140 | Calculation means |
| 150 | Output means |

BEST MODE FOR CARRYING OUT THE INVENTION

Figure 1:
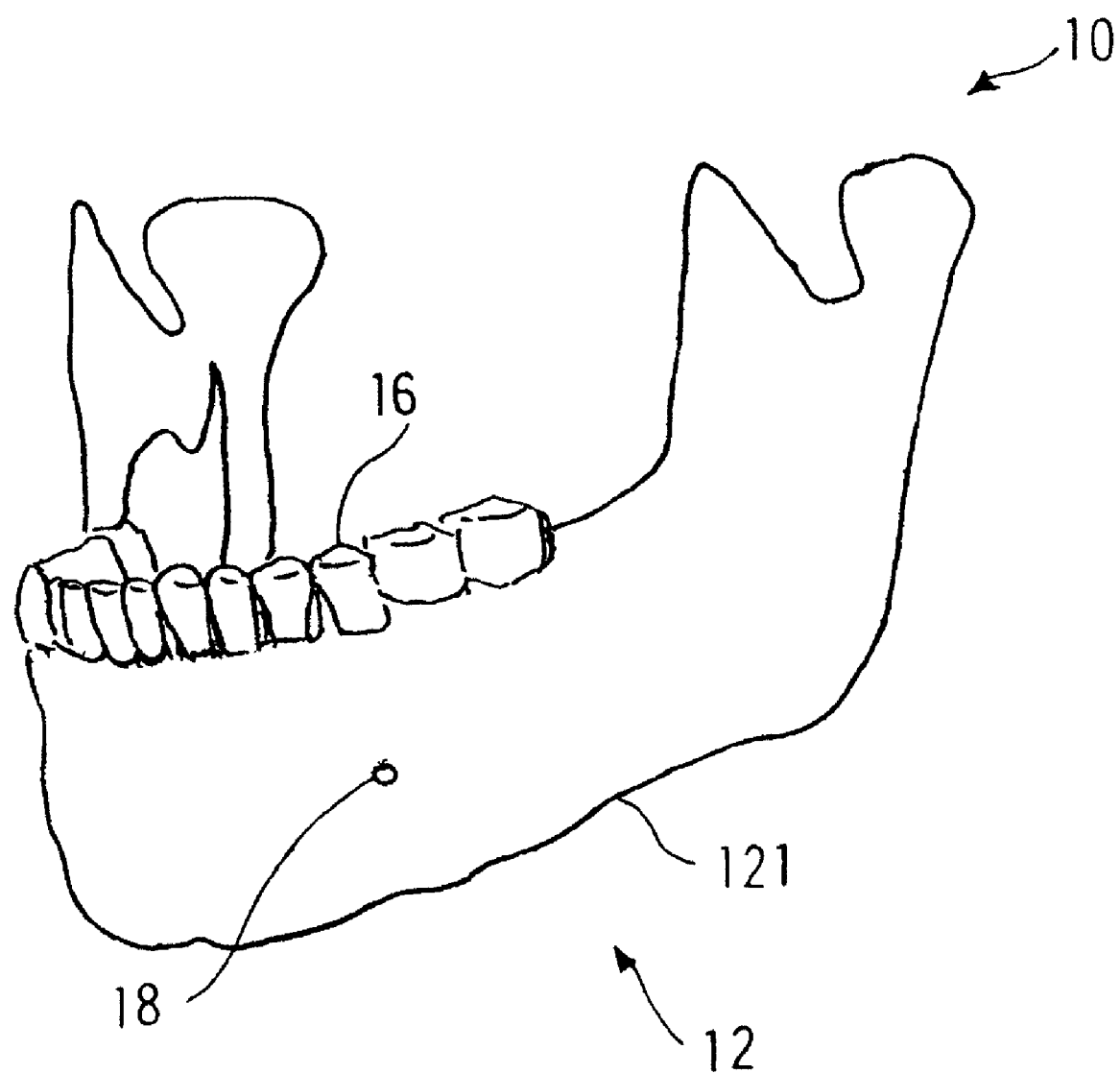
FIG. 1 is a schematic diagram of the mandible.
Figure 2:
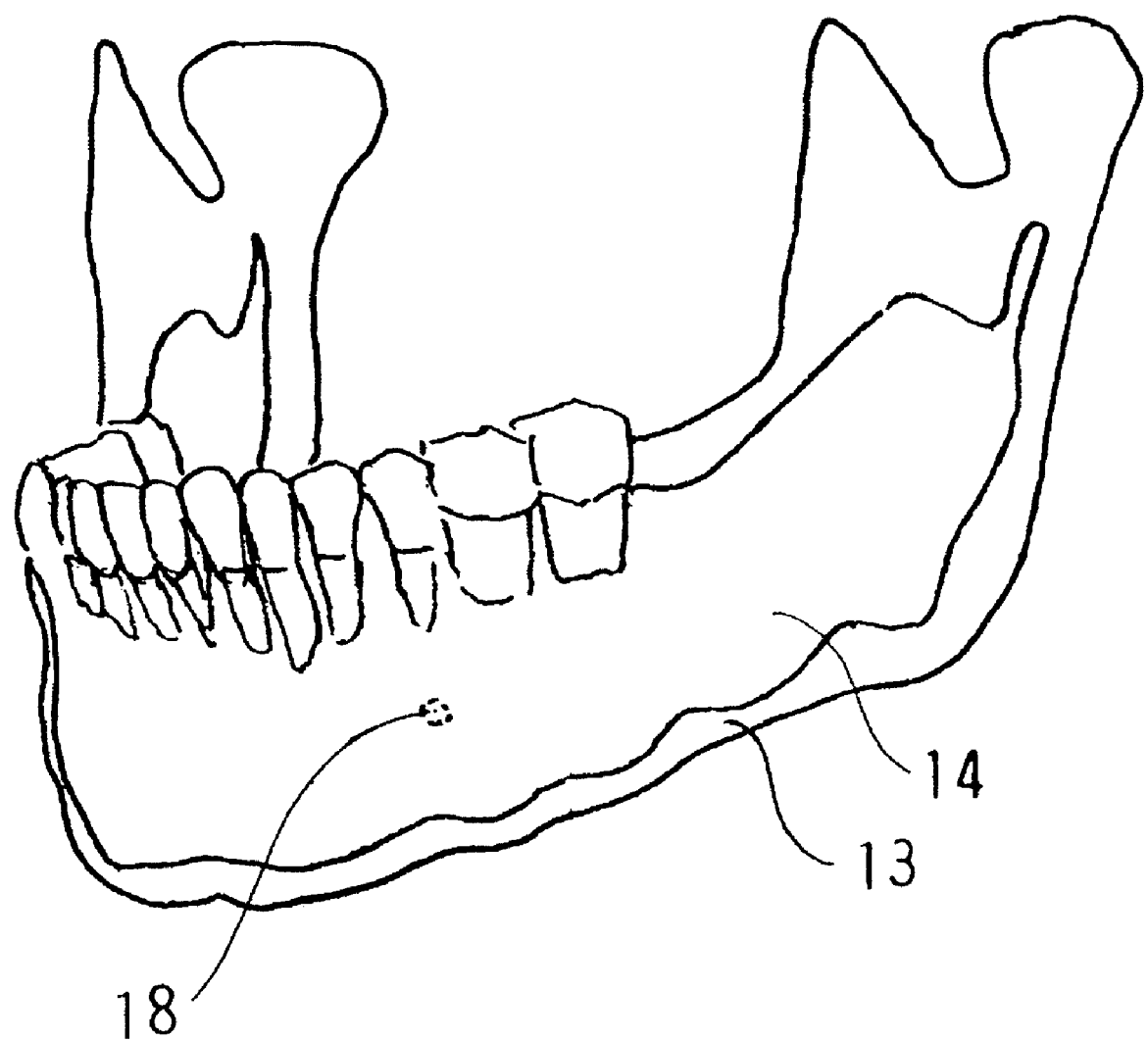
FIG. 2 is a cross-sectional view of FIG. 1.
Figure 3:
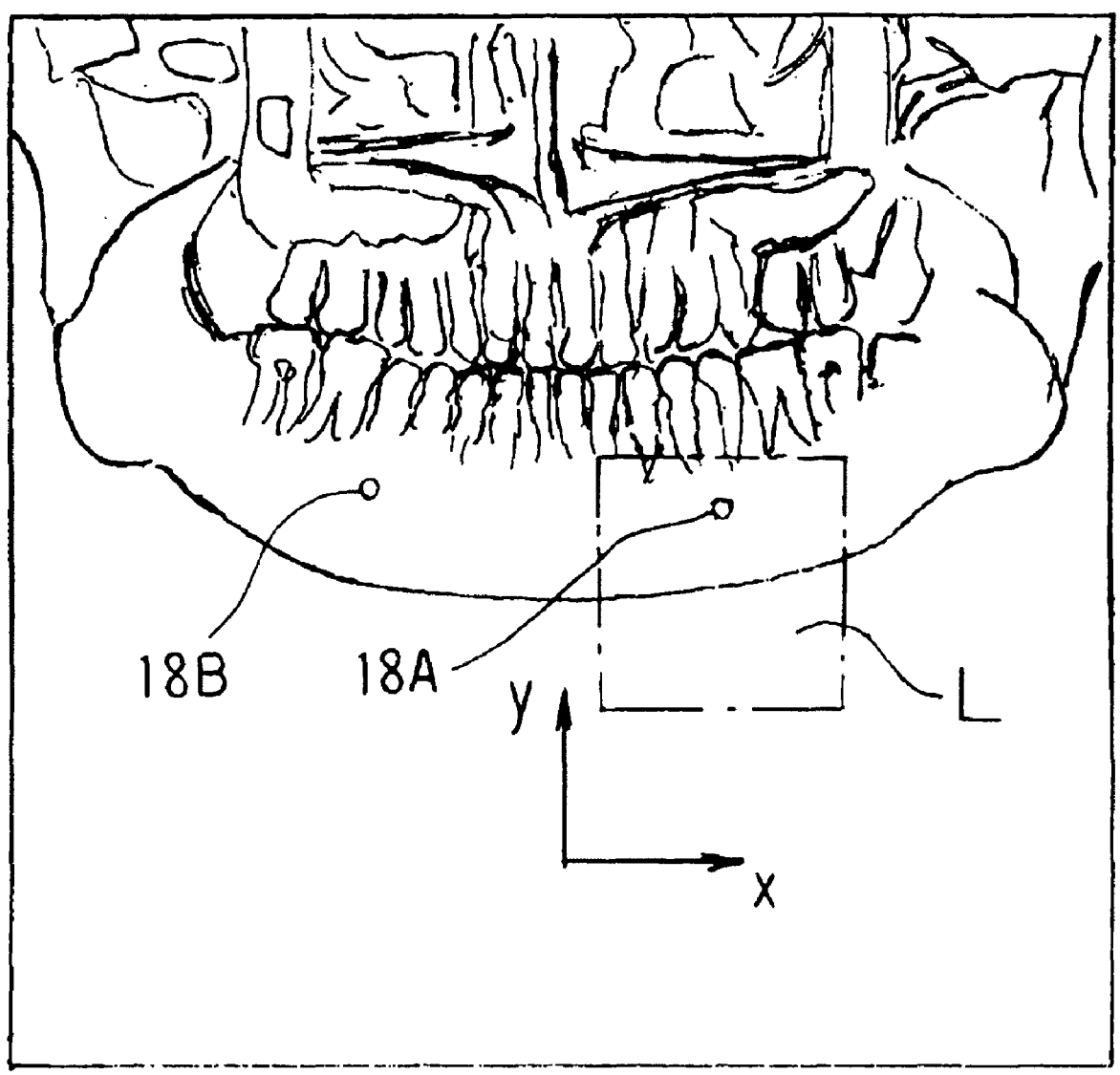
FIG. 3 is a schematic diagram of an example of a digitized panoramic radiograph.

An osteoporosis diagnosis support device according to the present invention will be described below. FIG. 1 is a perspective view of the subject mandible in the present invention. FIG. 2 is a cross-sectional view of FIG. 1. FIG. 3 is a schematic diagram of an example of panoramic radiographs taken in dental treatment. As shown in FIG. 1, the mandible bone 10 has the mental foramen 18 in the substantially middle portion of the mandibular base 121 of the mandible 12 and the second premolar tooth of mandible 16. As shown in FIG. 2, the mandible bone 10 has the cortical bone 13 and the cancellous bone 14 constituting the mandible 12, and the mandibular base 121 is formed by the outer edge of the cortical bone 13. The mental foramen 18 includes 18A and 18B in the symmetrical positions so as to interpose a center line therebetween.

Figure 5:
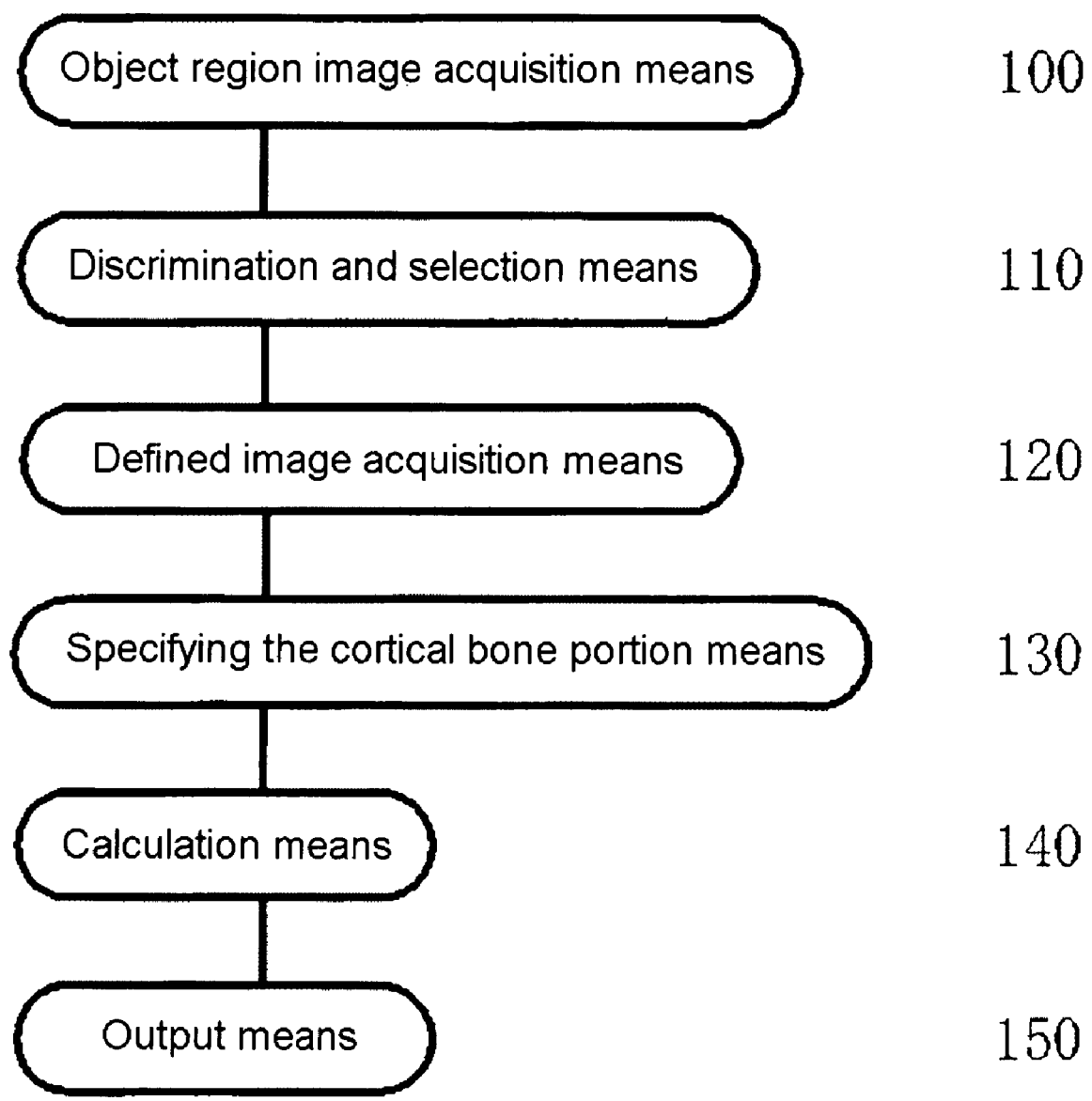
FIG. 5 is an explanatory view showing the configuration of an osteoporosis diagnosis support device according to the present invention.

As shown in FIG. 5, the osteoporosis diagnosis support device according to the present invention has the object region image acquisition means 100 for enhancing contrast of a mandible bone on digitized panoramic radiographs and extracting a portion of a mandible including a mental foramen and a mandibular base as an object region image; the discrimination and selection means 110 for discriminating between a background portion and the portion of a mandible from the object region image and acquiring, as a judgment region image, a portion in which the background portion is removed; the defined image acquisition means 120 for defining forms and outlines of a cortical bone and a cancellous bone constituting the mandible of the judgment region image; the means 130 for specifying a portion of the cortical bone on the image in which forms are defined; the calculation means 140 for determining the thickness of the cortical bone based on an outline constituting the mental foramen and the cortical bone defined by the respective means; and the output means for 150 outputting the determined thickness of the cortical bone.

The object region image acquisition means 100 enhances the contrast of the mandible bone 10 on digitized panoramic radiographs and extracting a portion of the mandible 12 including the mental foramen 18 and the mandibular base 121 as an object region image. For example, as shown in FIG. 3, the portion including the left mental foramen 18A from the digitized panoramic radiographs of the mandible bone 10 is extracted. In this case, two object region images including the left mental foramen 18A and the right mental foramen 18B can be extracted to judge the thickness of the cortical bone from the average value of the thickness of the cortical bone 13 obtained by the method described below.

As described above, in the present invention, the mental foramen 18 is used as the reference. The position of the mental foramen 18 present as described above is specified in a predetermined range. In addition, the contrast can be specified relatively easily unlike the cancellous bone 14 therearound. The skill and experience to specify it are required for the X-ray photograph. Therefore, first, the contrast of digitized panoramic radiographs of the mandible bone 10 is enhanced. Any known means can be used for the enhancement. For instance, the contrast between the mental foramen 18 observed in black and the cancellous bone 14 observed in whiter than that is enhanced. The mental foramen 18 is thus defined and the position of the mental foramen 18 can be easily specified.

The digitized panoramic radiographs of the mandible bone 10 may be previously made. Alternatively, it may be made by a means for digitalizing a panoramic radiograph film provided as an accessory in this osteoporosis diagnosis support device. Further, the entire panoramic radiographs taken on the film or a predetermined portion thereof may be digitalized.

As shown in FIG. 3, a portion of the mandible 12 including the mental foramen 18 and the mandibular base 121 is extracted as an object region image L from the contrast enhanced image. In this case, the xy coordinate system composes the y coordinate in the upward direction from the bottom, that is, in the direction from the foot to the head of a human body, when the panoramic radiographs are taken, and the x coordinate orthogonal thereto, and is preferably set in the above digital image. For instance, the xy coordinate system as shown in FIG. 3 is set in the digital image, and the range including the coordinate values of the mental foramen 18 and the sufficiently small y coordinate value is extracted as the object region image L.

Figure 4:
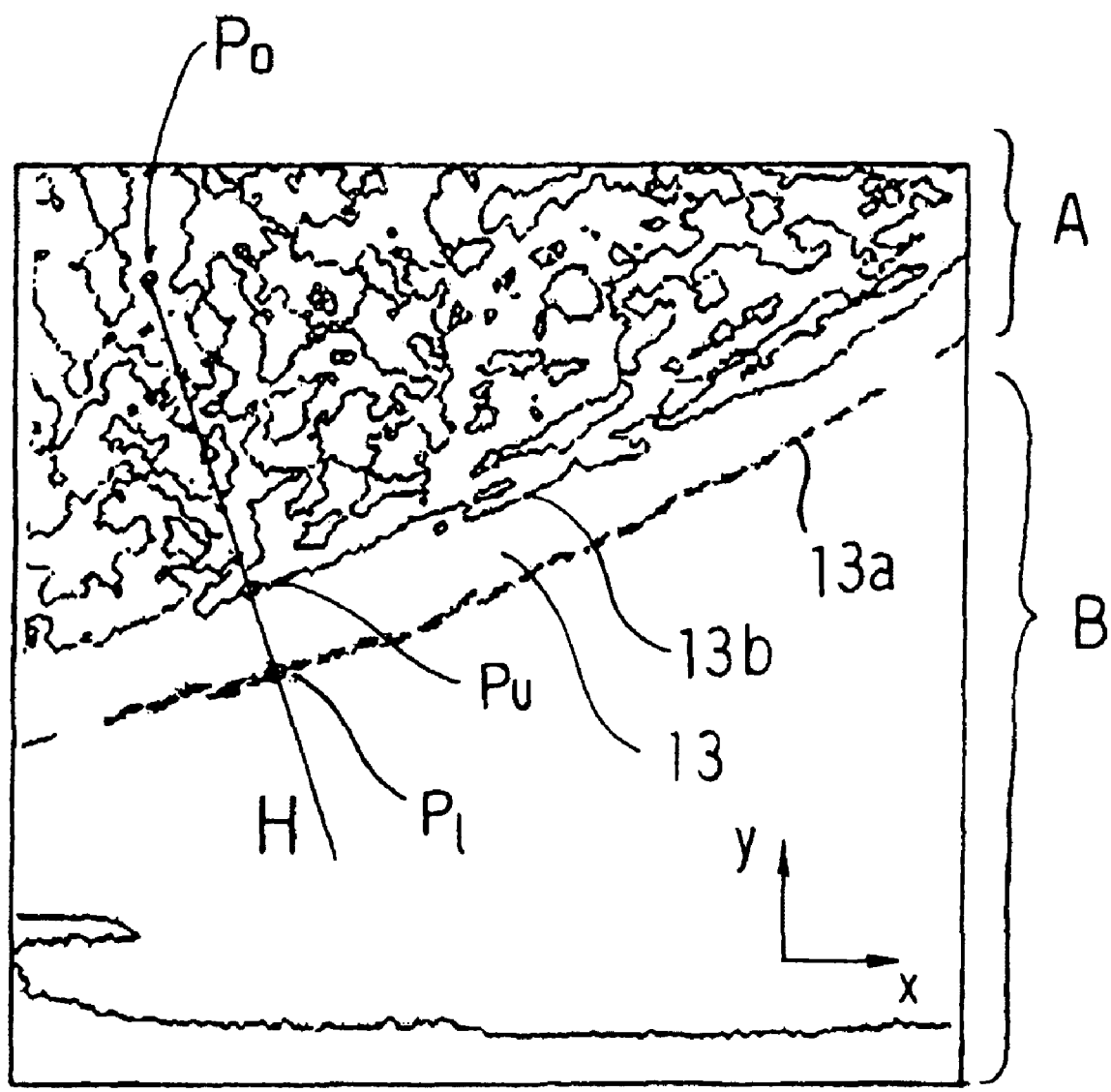
FIG. 4 is an explanatory view of measurement of the cortical bone using a judgment region image including the mental foramen in panoramic radiographs.

The discrimination and selection means 110 discriminates between the background portion and the portion corresponding to the mandible 10 from the object region image L and acquires, as a judgment region image, the portion A corresponding to the mandible 10 from which the background portion B is removed, as shown in FIG. 4. A binarization method is used as the method acquiring the judgment region image.

The binarization method comprises the following algorithms. That is, (1) a histogram of pixel values constituting an object region is created from the object region image L to sort, in ascending order, the pixel values appearing in the histogram. Then, there are introduced a cluster concept in which a group of pixels belonging to one pixel value constitutes one cluster and the concept of the distance between clusters defined by the product of intra-cluster dispersion and inter-cluster dispersion based on the cluster.

Figure 6:
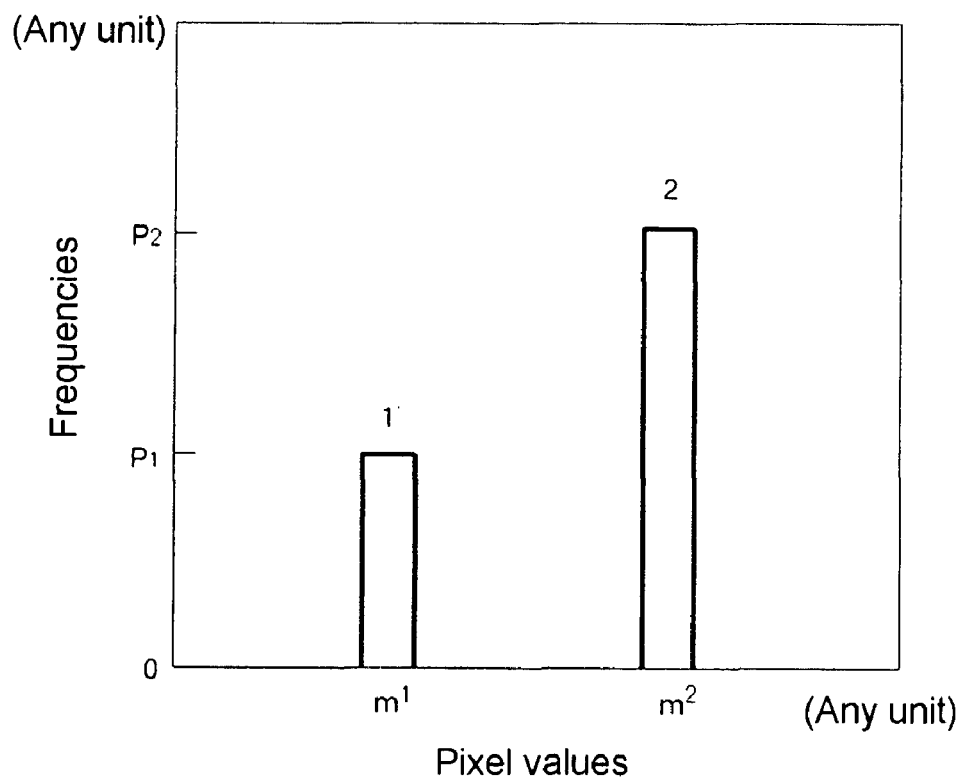
FIG. 6 is an explanatory view of a binarization method.

The binarization method will be specifically described using FIG. 6. The mean values of pixel values belonging to adjacent clusters 1 and 2 are m1 and m2, respectively, and the frequencies are P1 and P2. In the first stage in which cluster combination has not been performed by the following procedure, m1 is equal to the pixel value of the cluster 1 and m2 is equal to the pixel value of the cluster 2. The frequency may be the number of pixels or the proportion to the number of all pixels. Any unit can be adopted. This is ditto for the pixel value.

A mean M in which the mean values m1 and m2 of the pixel values are weighted by the number of pixels belonging to the respective clusters is determined: $M=(m1\times P1+m2\times P2)/(P1+P2)$. The inter-cluster dispersion D is $D=\{P1\times(m1-M)^2+P2\times(m2-M)^2\}/(P1+P2)$. The intra-cluster dispersion d is $d=\{P1\times(m1-M)^2+P2\times(m2-M)\}/(P1+P2)\}$. The distance between the cluster 1 and the cluster 2 is defined as D×d. Considering that the pixel values belonging to the cluster 1 are all m1 and the pixel values belonging to the cluster 2 are all m2, the inter-cluster dispersion D corresponds to dispersion of these pixel values. The intra-cluster dispersion d corresponds to dispersion of all the pixel values when both the clusters are combined.

Next, (2) the distance between two adjacent clusters is measured to combine the pair at the smallest distance into the cluster having a smaller pixel value. (3) The operation is repeated to advance cluster combination until there are two clusters. (4) In the two clusters finally obtained by the above operation, the pixel values belonging to the cluster having a larger pixel value are all replaced with 1 (white), and the pixel values belonging to the cluster having a smaller pixel value are all replaced with 0 (black). An image constituted by the pixel values belonging to 1 is the portion A corresponding to the mandible 10. An image constituted by the pixel values belonging to 0 is the background portion B. A judgment region image is thus acquired.

Figure 7:
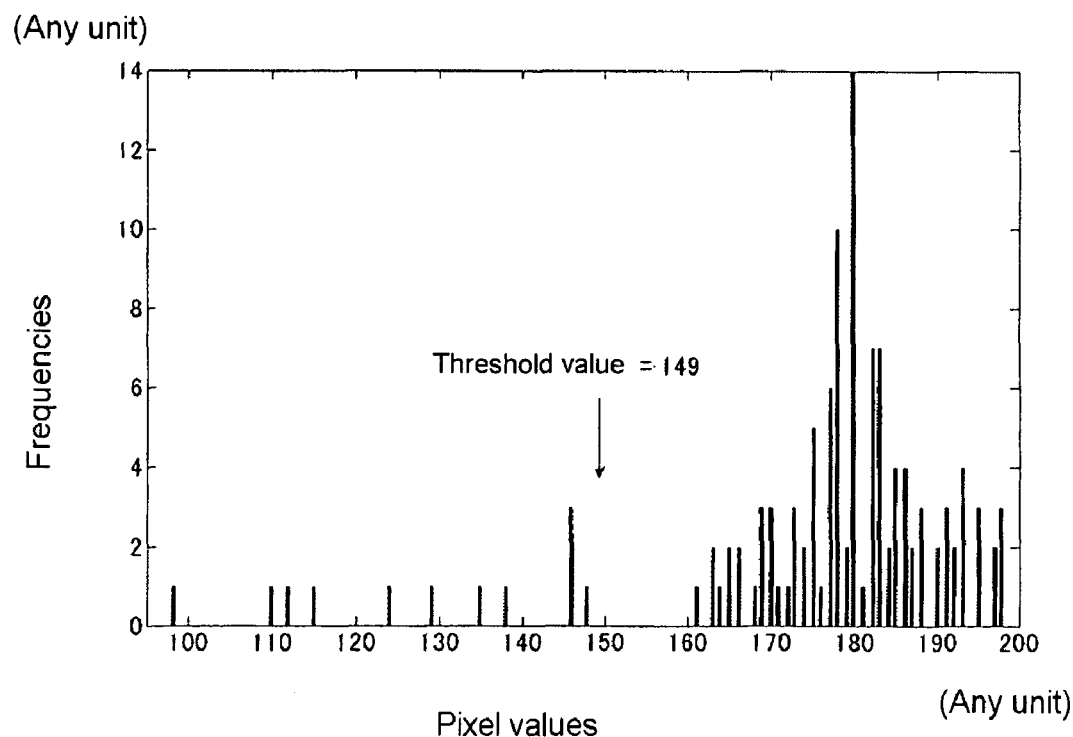
FIG. 7 is a graph showing an example of a histogram about pixel values applying the binarization method according to the present invention.

An example of a frequency distribution graph of the pixel values of the object region image L is shown in FIG. 7. In this example, the pixel value as a threshold value in which the pixel value is finally replaced with 0 or 1 by the binarization method is 149. The binarization method can obtain satisfactory results from the method by Otsu (N. Otsu, A threshold selection method from gray-level histograms, IEEE Trans. Systems Man and Cybernetics vol. SMC-9 no. 1 pp. 41-47 1986).

In the thus-acquired judgment region image, the forms and outlines of the cortical bone 13 and the cancellous bone 14 constituting the mandible 12 are defined by the defined image acquisition means 120. The definition can use any known method. For example, the form and outline of the cortical bone 13 and the cancellous bone 14 are defined by passing through a known low-pass filter and high-pass filter. The pixels belonging to the defined outline constitute the "outline" in the calculation means 140 for calculating the thickness of the cortical bone 13, which will be described below. The collective of the pixels belonging to the outline is a collective of pixels in which a pixel value called an edge is abruptly changed in imaging processing.

As for the defined image acquired by the defined image acquisition means 120, the image portion belonging to the cortical bone 13 is specified by the means 130 for specifying the cortical bone portion. The means 130 for specifying the cortical bone portion may observe the cortical bone portion by a monitor displaying the defined image in which the cortical bone 13 and the cancellous bone 14 can be definitively discriminated with human eyes. For instance, a operator may specify the cortical bone portion using a mouse or a light pen. In the case of an osteoporosis patient whose thickness of the cortical bone is very thin and is below several mm, the thickness of the cortical bone can be measured with high accuracy. The structure on the software program can be simplified and measurement time can be shortened. The cortical bone portion can be specified by the program.

Next, the thickness of the cortical bone 13 is determined by the calculation means 140 as follows. The xy coordinate system shown in FIG. 3 is set on the judgment region image. There is set the xy coordinate system composing the y coordinate in the upward direction from the bottom, that is, in the direction from the foot to the head of a human body, when panoramic radiographs are taken, and the x coordinate orthogonal to the y coordinate so that its positive direction is the direction moved away from the edge of the jaw. (1) With one point belonging to the specified cortical bone 13 as a start point, a straight line is extended in the direction in which the x coordinate is increased in parallel with the y coordinate, and the pixel at the point crossing the outline is stored in a storage area.

Next, (2) the pixel on the outline within 8 pixels near each pixel in the storage area is stored in the storage area. (3) Further, the pixel on the outline within 8 pixels near each pixel is stored in the storage area. Such operation is performed one after another and is continued until there are no pixels to be stored in the storage area or the number of pixels in the storage area is the initially set value. For instance, the maximum number of pixels which can be stored in the stack can be about 1000. Then, (4) a pixel group A in the storage area forms the outer edge of the cortical bone. When there are pixels in the storage area having the same y coordinate, the pixel having the largest x coordinate forms the outer edge of the cortical bone.

Further, (5) with one point belonging to the specified cortical bone as a start point, a straight line is extended in the direction in which the x coordinate is decreased in parallel with the y coordinate, and a pixel at the point crossing the outline is stored in the storage area to perform the same operation as (2) and (4) so that a pixel group B finally stored in the storage area forms the inner edge of the cortical bone.

Next, (6) a regression line based on each pixel in the pixel group A and a pixel therenear is determined. The number of pixels used for determining the regression line can be, e.g., about 50 near a noted pixel. This can solve the problem that the inner edge of the cortical bone 13 of an osteoporosis patient is sponge-like so that the inner edge portion cannot be easily specified.

Finally, (7) an angle formed by a straight line connecting the mental foramen and each pixel in the pixel group A and the regression line based on the pixel is determined to specify, as an outer edge point, the pixel in which the angle is closest to 90°. (8) In the pixel group B within a fixed distance from a straight line connecting the outer edge point and the mental foramen, the point in which the distance between it and the outer edge point is smallest is referred to an inner edge point. Then, (9) the length from the outer edge point to the inner edge point is referred to the thickness of the cortical bone 13. The term "within a fixed distance" can be, e.g., about 7 pixels.

The above procedure will be described below using FIG. 4. In FIG. 4, the outer edge of the cortical bone 13 is 13$a$ and the inner edge thereof is 13$b$. There is determined a straight line $P_0H$ which is a straight line passing through the mental foramen 18 and is closest to the perpendicular line of the outer edge of the cortical bone 13 (represented as a curve connected to the regression line). A cross point $P_1$ of the straight line $P_0H$ and the regression line 13$a$ is referred to the outer edge point. In the pixels on the inner edge within a fixed range from a straight line $P_0P_1H$, a point $P_u$ in which the distance between it and the outer edge point is smallest is determined. The thickness of the cortical bone 13 is determined from the length of a straight line $P_1P_u$.

The thus-determined thickness of the cortical bone 13 is outputted from the output means 150 such as a voltage recording meter or a monitor. Based on the output of thickness of cortical bone 13, it is determined whether osteoporosis or not. In this case, the output means 150 preferably comprises an osteoporosis database, and the osteoporosis-identification-judgment-means by comparing data stored in the database with the thickness of the cortical bone 13. Using this, diagnosis can be performed with high accuracy.

Table 1 shows results obtained by actually performing osteoporosis diagnosis based on data of 100 panoramic radiographs using the osteoporosis diagnosis support device according to the present invention. In Table 1, the section of lumbar vertebrae standard shows the results of sensitivity and the like obtained by visual judgment by one technician with abundant experience of medical practice and the results of sensitivity and the like obtained by automatic judgment using the osteoporosis diagnosis support device according to the present invention, with respect to the diagnosed results by lumbar vertebrae bone density data using the DXA method (these results are Gold standard). The upper stand shows a 95% reliable section and the lower stand shows the lower limit and the upper limit of the reliable section. The section of thighbone standard shows the same results as the lumbar vertebrae standard with respect to the diagnosed results from lumbar vertebrae examination using the DXA method.

According to Table 1, based on the lumbar vertebrae standard, the sensitivities were 92.0 in visual judgment and 88.0 in automatic judgment. Based on the thighbone standard, the sensitivities were 87.5 in visual judgment and 87.5 in automatic judgment. The sensitivities were high in both visual judgment and automatic judgment. The sensitivity in automatic judgment was found to be almost the same as that in visual judgment. This was ditto for the specificity. The medical statistical numerical values of the automatic judgment results using the osteoporosis diagnosis support device according to the present invention and the visual judgment results by one technician with abundant experience of medical practice were well matched with each other. The automatic judgment results using the osteoporosis diagnosis support device according to the present invention show that osteoporosis diagnosis can be performed at high accuracy.

Note that the technician performing visual judgment in Table 1 judged the data of 100 panoramic radiographs twice. Both inter-observer reproducibility and intra-observer reproducibility were moderate or almost perfect. The visual judgment results by the technician were found to be reliable.

The threshold value of whether it was osteoporosis or not was set in such a manner that the sensitivities in visual evaluation and automatic support were about 90% based on the sensitivity and specificity curve (ROC curve).

The invention claimed is:

1. An osteoporosis diagnosis support device, comprising:
    an object region image acquisition unit for acquiring image data of panoramic radiographs including a cortical bone;
    an outline acquisition unit for acquiring a pixel group A forming an outer edge of the cortical bone in the image data and a pixel group B forming an inner edge of the cortical bone in the image data;
    a calculation unit for using, as a reference point, a specific point in the image data and is different from the pixel groups A and B to calculate a distance between a specific pixel in the pixel group A and a pixel in a predetermined range in the pixel group B; and
    an output unit for outputting the distance determined by the calculation unit as a thickness of the cortical bone.

2. The osteoporosis diagnosis support device according to claim 1, wherein the reference point is the mental foramen of the mandible.

3. The osteoporosis diagnosis support device according to claim 1, wherein the calculation unit comprises:
    an outer edge point specification unit for specifying, as an outer edge point, the specified pixel, in which an angle formed by a regression line based on one pixel pixel group A and a pixel therenear and a straight line connecting the reference point and the specific pixel is closest to 90°;
    an inner edge point specification unit specifying, as an inner edge point, the pixel group B within a fixed distance from a straight line connecting the reference point and the outer edge point; and
    a length calculation unit calculating the distance from the outer edge point to the inner edge point.

4. The osteoporosis diagnosis support device according to claim 3, wherein the thickness of the cortical bone is the smallest value of the distance determined by the calculation unit.

5. The osteoporosis diagnosis support device according to claim 3, wherein the thickness of the cortical bone is the largest value of the distance determined by the calculation unit.

6. The osteoporosis diagnosis support device according to claim 3, wherein the thickness of the cortical bone is the average value of the distance determined by the calculation unit.

TABLE 1

|  |  | Sensitivity | Specificity | Positive success rate | Negative success rate | Degree of accuracy | Likelihood ratio |
|---|---|---|---|---|---|---|---|
| Lumbar vertebrae standard | Visual judgment | 92.0<br>81.4-100.0 | 60.0<br>48.9-71.1 | 43.4<br>30.1-56.7 | 95.7<br>90.0-100.0 | 68.0<br>58.9-77.1 | 2.3<br>1.7-3.1 |
|  | Automatic judgment | 88.0<br>75.3-100.0 | 58.7<br>47.5-69.8 | 41.5<br>28.2-54.8 | 93.6<br>86.6-100.0 | 66.0<br>56.7-75.3 | 2.1<br>1.6-2.9 |
| Thighbone standard | Visual judgment | 87.5<br>74.3-100.0 | 64.8<br>53.7-75.9 | 45.7<br>31.3-60.0 | 93.9<br>87.2-100.0 | 70.5<br>61.4-79.7 | 2.5<br>1.8-3.5 |
|  | Automatic judgment | 87.5<br>74.3-100.0 | 56.3<br>44.8-67.9 | 40.4<br>27.0-53.7 | 93.0<br>85.4-100.0 | 64.2<br>54.6-73.9 | 2.0<br>1.5-2.7 |

7. An osteoporosis diagnosis support method, comprising:
    an object image acquisition step for acquiring image data of panoramic radiographs including a cortical bone:
    an outline acquisition step for acquiring a pixel group A forming an outer edge of the cortical bone in the image data and a pixel group B forming an inner edge of the cortical bone in the image data:
    a calculation step using, as a reference point, a specific point which is a point in the image data and is different from the pixel groups A and B to calculate a distance between a specific pixel in the pixel group A and a pixel within a predetermined range in the pixel group B; and an output step for outputting the distance determined by the calculation step as a thickness of the cortical bone.

8. A computer-readable medium having instructions stored thereon, such that when the instructions are read and executed by a processor, is configured to perform the steps of acquiring image data of panoramic radiographs including a cortical bone;

acquiring a pixel group A forming an outer edge of the cortical bone in the image data and a pixel group B forming an inner edge of the cortical bone in the image data;

calculating a distance between a specific pixel in the pixel group A and a pixel in a predetermined range in the pixel group B by using, as a reference point, a specific point which is a point in the image data that is different from pixel groups A and B; and outputting the distance determined by the calculation program as a thickness of the cortical bone.

* * * * *